United States Patent [19]

Nelson

[11] Patent Number: 4,800,765

[45] Date of Patent: Jan. 31, 1989

[54] GRAIN DRILL AND PROBE MECHANISM

[76] Inventor: Eugene E. Nelson, 101 South Skyline Dr., Mankato, Minn. 56001

[21] Appl. No.: 31,088

[22] Filed: Mar. 26, 1987

[51] Int. Cl.$^4$ .......................... G01N 1/08; G01N 1/16
[52] U.S. Cl. ................................. 73/864.64; 73/863.86
[58] Field of Search ........... 73/863.85, 863.86, 864.43, 73/864.64, 866.5

[56] References Cited

U.S. PATENT DOCUMENTS

| | | |
|---|---|---|
| 1,966,712 | 7/1934 | Fisher et al. |
| 3,365,952 | 1/1968 | Wang |
| 3,424,009 | 1/1969 | Reichenstein |
| 4,037,476 | 7/1977 | McCrabb ...................... 73/864.64 X |
| 4,072,059 | 2/1978 | Hamilton ...................... 73/864.64 X |
| 4,179,930 | 12/1979 | Chrisp ............................. 73/864.64 |
| 4,283,946 | 8/1981 | Bowser et al. ................ 73/864.64 X |
| 4,738,142 | 4/1988 | Morgan ............................ 73/864.64 |

Primary Examiner—Tom Noland
Attorney, Agent, or Firm—Wm. Bruce Day

[57] ABSTRACT

A drill and probe mechanism is adapted for use in grain bins and extends down deep into the body of grain to either retrieve a grain sample or deposit fumigation pellets. The drill portion of the mechanism includes a hydraulic pump providing power for a reversible hydraulic rotary head and separate screw. Lengths of drill string connect to the rotary head and the screw pushes the rotating drill string downward into the body of grain. A probe connected to the end of the drill string includes a tubular container body with doors that are opened and closed by selective clockwise and counterclockwise rotation of the drill string. Various types of probes are utilized, including one that merely collects grain for sampling and another that dispenses fumigant pellets.

9 Claims, 4 Drawing Sheets

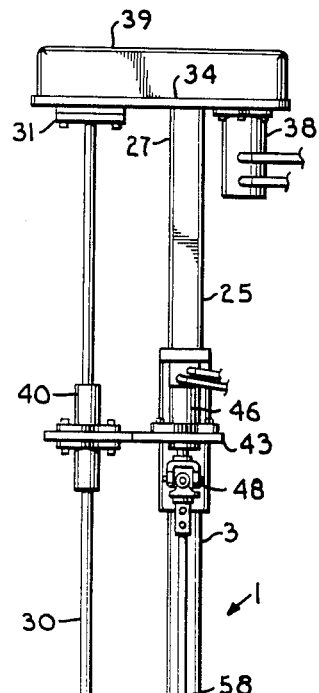
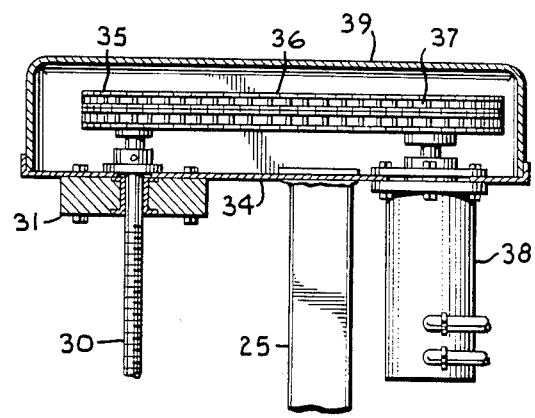
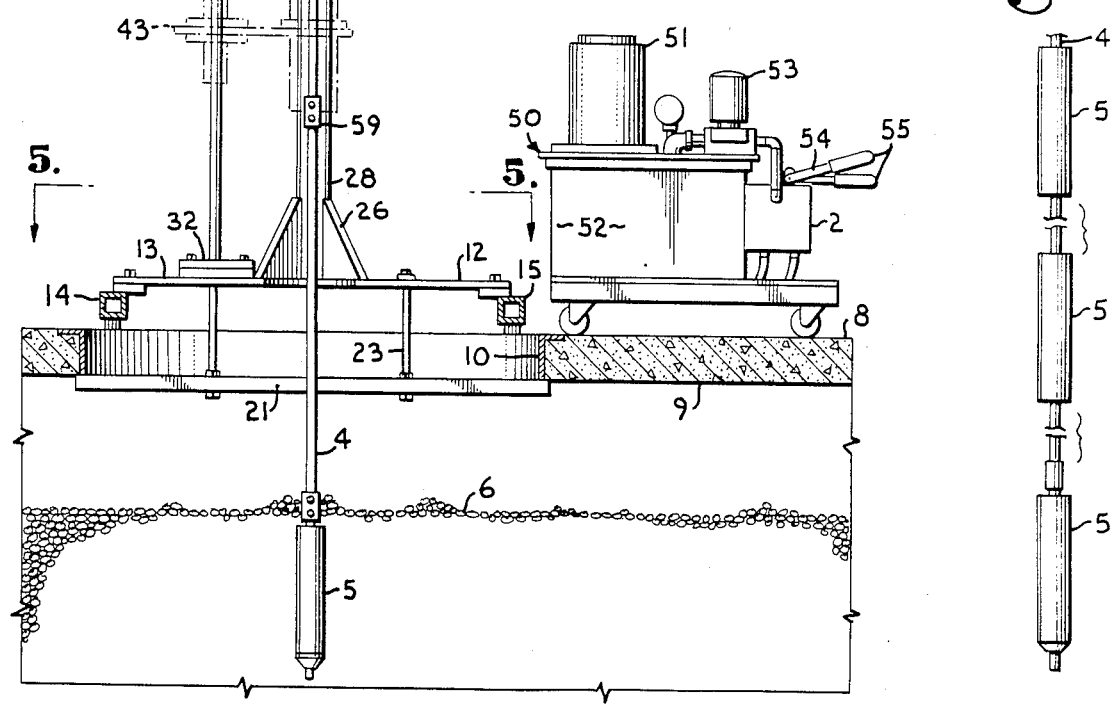

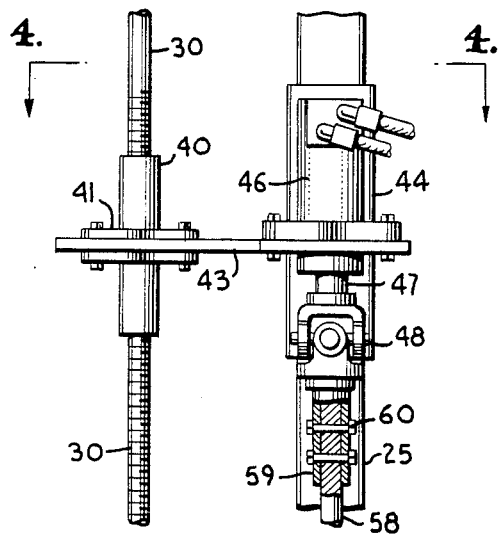
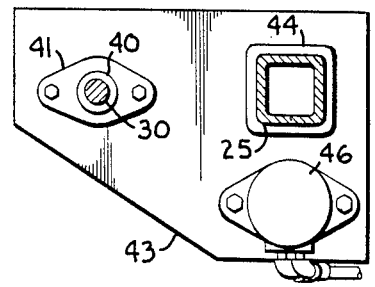
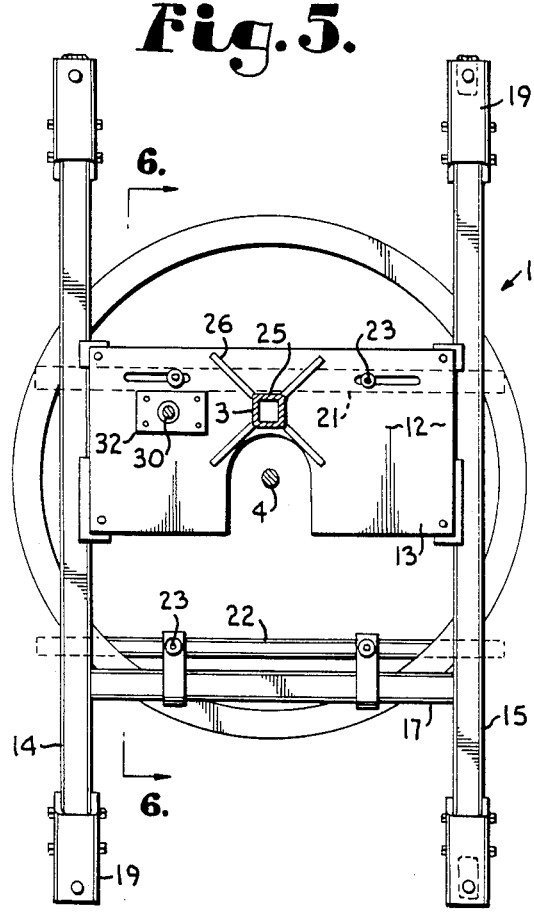
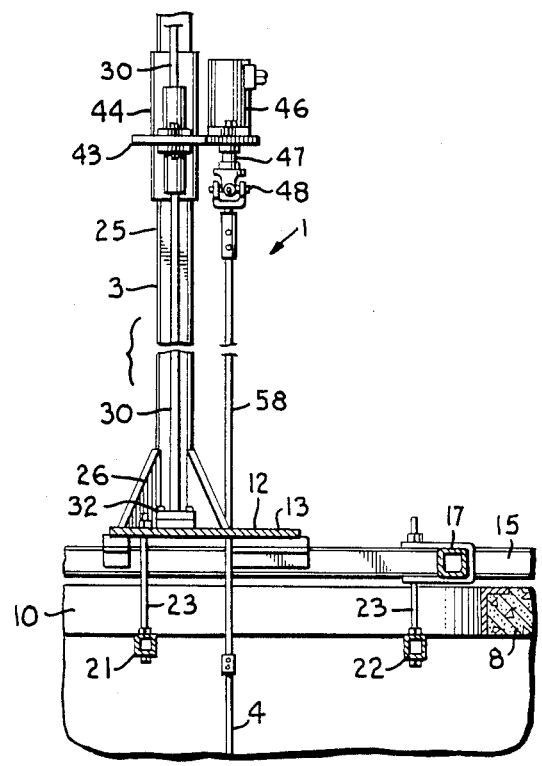

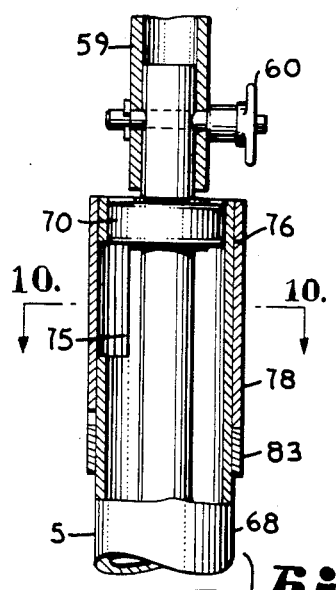
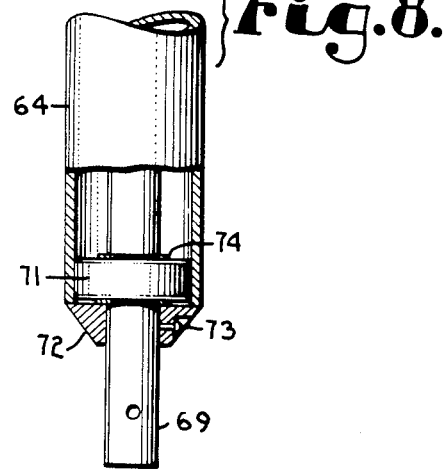
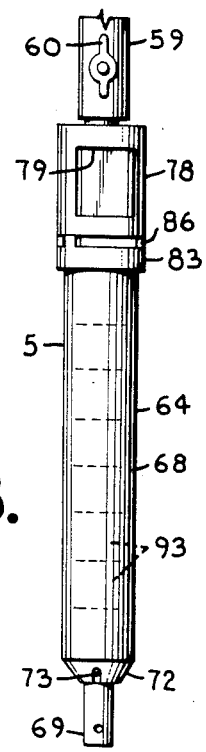
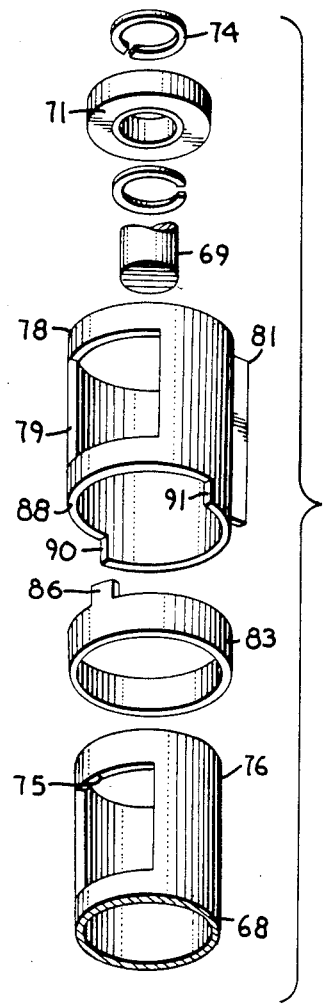
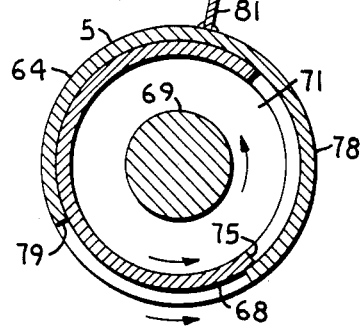
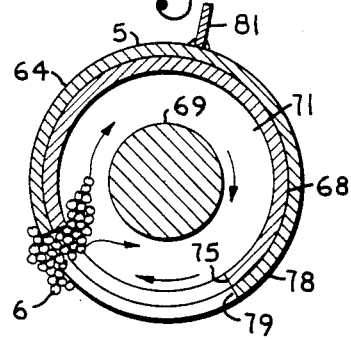
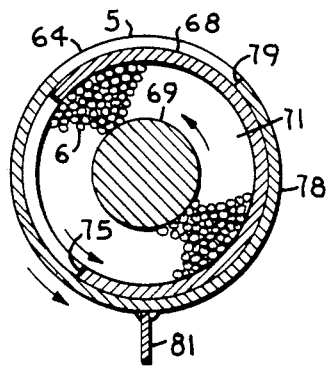

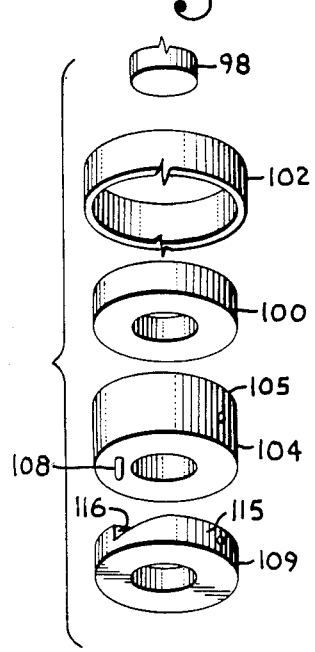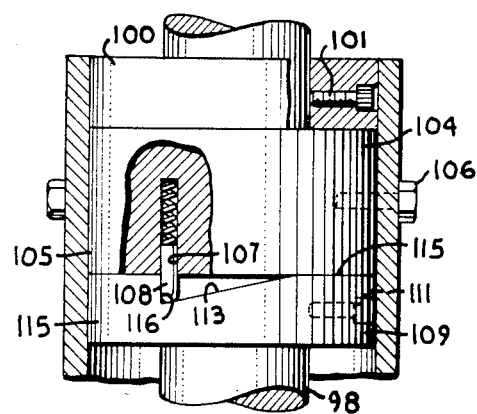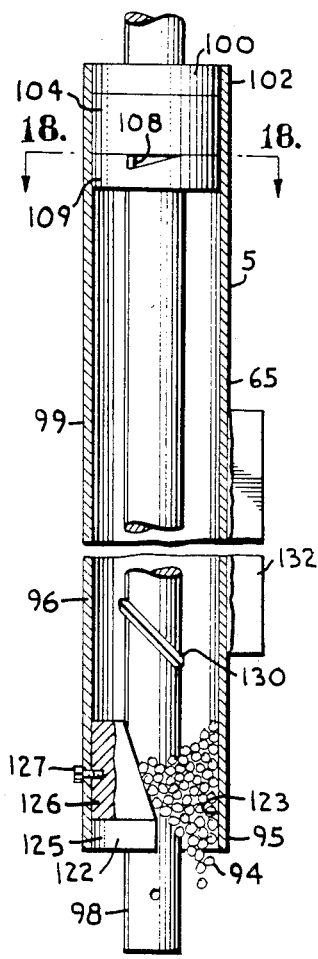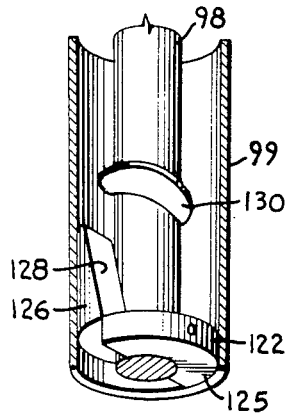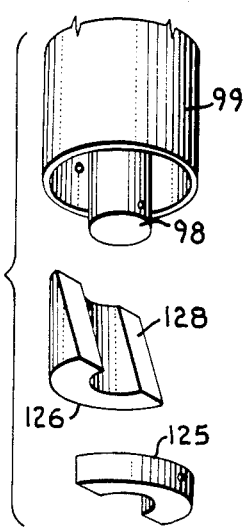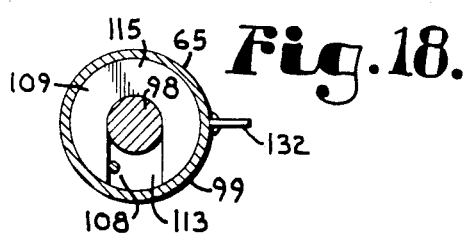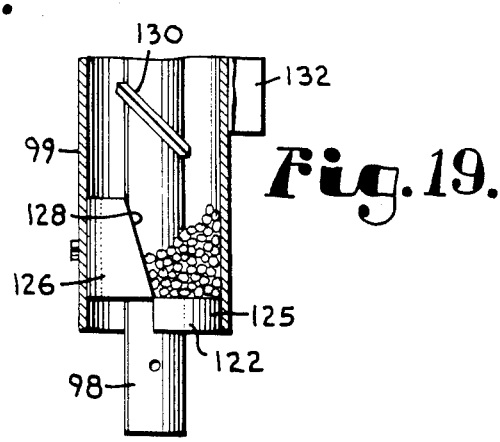

GRAIN DRILL AND PROBE MECHANISM

FIELD OF THE INVENTION

This invention relates to a probe mechanism for sampling grain, and in particular, to a combination drill and sampling mechanism designed to carry the probe down to great depths within a body of grain or other particulate material.

BACKGROUND OF THE INVENTION

Grain is ordinarily stored in large, vertically extending bins until sold for processing. Within the system of grain distribution, the farmer may have several small bins to provide limited storage for a single year's crop, so that it can be sold at price advantageous times. Grain does not tend to remain in these storage bins for long and may be sold at the time of harvest, or within a relatively short period thereafter, to a country elevator. The typical country elevator is located along a rail line in the small towns or cities that serve the farmer. Grain is trucked to the country elevator and conveyed into the storage bins. The country elevator often has only minimal storage capability and consists of less than ten bins, each of which is normally between sixty to one hundred and thirty feet high. Depending upon the availability of railroad cars, river barges or other suitable means of large scale surface transportation, grain is taken from the county elevator to a terminal elevator where it remains until sold.

The typical terminal elevator operation consists of ten or more large vertical bins and may store over a million bushels of grain for several years until sold for processing. Because of the extreme value of this grain inventory, the quality of the grain must be carefully monitored. The typical terminal elevator operation utilizes temperature and moisture monitoring systems and takes such careful steps to control rodent and insect populations, that with a well run elevator, the presence of rodents is uncommon. For insects and mold, the situation becomes more complex. For mold or fungi problems, the bin must be emptied and circulated to an empty bin through a series of bottom conveyors, lift conveyors and top conveyors, sampled by hand and visually inspected.

For insect infestation, the situation is the same. If insects are noted, then the usual course of action has been to transfer the grain to another bin and while the grain is being transferred, to inspect it, and as the grain is being deposited in the second bin, intermix fumigant material with it.

The cost of moving the grain, that is, emptying the bin and putting the grain into another bin, is expensive and when figuring labor costs, wear and tear on equipment, and the costs of electrical energy, the present cost to move the grain is $1,000.00 to $1,500.00, depending upon the bin capacity. Attempts have been made previously to construct probes to sample the grain in the bins, rather than moving the grain, when problems are suspected or for regular inspection. Sampling devices have previously been made in the form of augers which employ a tube with external flytes designed to screw into a body of grain and with an internal auger designed to bring the grain to the surface for inspection. This type of device has generally proven to be unsatisfactory, for the system is subject to frequent failures and the device may be only able to extend to thirty to forty feet at best.

The present invention is designed to provide a deep probe which may extend down as much as eighty to one hundred and thirty feet, or to the depth of the highest known elevators. The instant drill and probe mechanism is effective in extending down deep into the bin at a selected depth and removing a sample for inspection from that depth. Various probes can be connected to the end of the drill mechanism whereby not only can a sample be retrieved, but fumigant pellets or granules can be dispensed at the selected depth and the probe and drill mechanism removed. Although this invention is not foreseen to entirely negate the necessity for moving the grain from bin to bin, it is foreseen that this invention will significantly reduce the frequency at which grain is moved, as the major problems of sampling can be accomplished while the grain is in the bin.

OBJECTS OF THE INVENTION

The principal objects of the present invention are: to provide a grain drill and probe mechanism adapted for deep drilling into grain bins; to provide such a grain drill and probe mechanism in which the drill has independent rotation and extension in the body of grain; to provide such a grain drill and probe mechanism in which lengths of the drill string are easily handled and connectible for deep drilling operations; to provide such a grain drill and probe mechanism in which the probe retrieves samples of grain from selected depths within the bin; to provide such a grain drill and probe mechanism having probes which retrieve grain samples and dispense fumigant pellets at selected depths; and to provide such a grain drill and probe mechanism which is relatively inexpensive, sturdy and efficient in use and particularly well adapted for the intended purpose.

Other objects and advantages of this invention will become apparent from the following description taken in connection with the accompanying drawings wherein are set forth by way of illustration and example, certain embodiments of this invention.

DESCRIPTION OF THE DRAWINGS

FIG. 1 is an elevational view showing a grain drill and probe mechanism embodying the present invention and depicted mounted upon the floor of a grain bin.

FIG. 2 is an enlarged, fragmentary view of a top portion of the grain drill and probe mechanism.

FIG. 3 is an enlarged, fragmentary view of a rotary head portion of the mechanism.

FIG. 4 is a sectional view taken along lines 4—4, FIG. 3.

FIG. 5 is a top plan view of the grain drill and probe mechanism.

FIG. 6 is a side elevational view of the grain drill and probe mechanism.

FIG. 7 is an elevational view of a sampler probe which is drilled into the grain bin.

FIG. 8 is an enlarged, fragmentary view of the sampler probe.

FIG. 9 is a perspective, disassembly view of the top portion of the sampler probe.

FIG. 10 is a sectional view taken along lines 10—10, FIG. 8.

FIG. 11 is a sectional view taken after FIG. 10 and showing relative rotation of parts to open a door and admit grain for sampling.

FIG. 12 is a sectional view after FIG. 11 showing relative rotation of parts and closing of the door to secure the sampled grain within the probe.

FIG. 13 is an elevational, fragmentary view of a fumigant dispenser probe.

FIG. 14 is an enlarged, fragmentary view of a top portion of the dispenser probe.

FIG. 15 is a perspective, disassembly view of the parts shown in FIG. 14.

FIG. 16 is a fragmentary view of the lower end portion of the dispenser probe.

FIG. 17 is a disassembly view of the parts shown in FIG. 16.

FIG. 18 is a sectional view taken along lines 18—18, FIG. 13.

FIG. 19 is a fragmentary view of the lower portion of the dispenser probe.

FIG. 20 is a diagrammatic view of a series of probes connected in a drill string for sampling or dispensing pellets.

DESCRIPTION OF THE PREFERRED AND ALTERNATE EMBODIMENTS

As required, detailed embodiments of the present invention are disclosed herein, however, it is to be understood that the disclosed embodiments are merely exemplary of the invention which may be embodied in various forms, therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail,

The reference numeral 1, FIGS. 1, 5 and 6, generally indicates a grain drill and probe mechanism embodying the present invention. The mechanism 1 includes a drill power means 2 which operates a drill rig 3 to rotate and extend or retract a drill string 4 and position a probe 5 within a body of grain 6.

In the illustrated example, the grain drill and probe mechanism 1 is particularly adapted for use on the floor 8 of a grain elevator. What is termed the floor is in fact the upper ceiling or top of the grain bin. Normally, an elevator contains at least several grain bins and the connected upper ceilings form a continuous floor located above the building ground surface some eighty to one hundred and fifty feet high. Commonly, an upper shed arrangement covers the elevator floor 8 and the associated conveyors that run along the top of the conveyor floor and which are routed to move grain into the elevator bins. Each bin 9 includes a bin opening 10 normally protected by a man-hole cover (not shown). The cover is removed when grain flow is routed into the bin 9 and for purposes of affixing the grain drill and probe mechanism 1 above the bin.

In the illustrated example, FIGS. 1, 5 and 6, the drill rig 3 includes a base 12 including a foot plate 13 extending between parallel, spaced support beams 14 and 15 which are connected by a cross beam 17 and the foot plate 13. The support beams 14 and 15 have rolling castors 19 at their opposite ends so that the drill rig 3 may be easily moved from bin to bin. To maintain the base 12 affixed to the bin floor 8 about the opening 10, base clamp bars 21 and 22 extend across the underside of the opening 10 generally under the cross beam 17 and the foot plate 13 and are connected thereto by bolts 23 to draw the clamp bars 21 and 22 tightly upwardly whereby their ends snugly squeeze the margins of the bin opening 10.

An upright post 25 extends from the foot plate 13 with gussets 26 providing support. The post 25 is preferably of square beam configuration and includes upper and lower ends 27 and 28. A screw rod 30 extends parallel to the post 25 and has opposite ends supported in upper and lower bearing blocks 31 and 32. The rod 30, at the upper bearing block 31, and the post 25, at its upper end 27, are secured to a transmission box plate 34, FIGS. 1 and 2. The rod 30 extends upwardly of the box plate 34 and terminates in a transmission assembly including a sprocket 35 connected by a transmission chain 36 to a motor sprocket 37 driven by a motor 38 for selective directional rotation of the screw rod 30. In the illustrated example, the motor 38 is a hydraulic motor although other modes of power means may be utilized as required. A cover 39 extends over the transmission assembly.

A traveling nut assembly 40 is mounted on the screw rod 30 and includes a bearing support 41 and a traveling plate 43, FIG. 3. The traveling plate 43 extends from the screw rod 30 and around the post 25, providing a collar 44 slidably engaging the post 25. A motor 46 is mounted to the traveling plate 43 forward of the post 25 and a motor shaft 47 extends downwardly and through the traveling plate 43 and terminates in a universal joint connection 48. As set forth below, lengths of the drill string 4 are attached to the universal joint connection 48.

In the illustrated example, the drill power means 2, powering the motors 38 and 46, is a portable hydraulic power unit 50 including an electrical motor 51 powering a pump (not shown) located within a reservoir tank 52 and having conduits leading to an oil filter 53 and a control box 54 with appropriate control levers 55. The power unit 50 is a high pressure unit and preferably provides a 3,000 psi system. Operation of the control levers 55 routes fluid to the motors 38 and 46 for rotation in either direction, as selected by the control levers 55.

Manipulation of the control levers 55 causes selective directional rotation of the motors 38 and 46. Rotation of the motor 38 causes rotation of the screw rod 30 and selected upward or downward movement of the traveling nut assembly 40 on the rod 30. As the traveling nut assembly 40 moves up and down, the traveling plate 43 moves commensurately, sliding on the post 25 and carrying the motor 46 therewith. Selected directional rotation of the motor 46, through manipulation of the control levers 55, causes spinning of the U-joint connection 48 and its connected drill string 4. As such, the spinning of the drill string 4 is not intended to act as a screw or auger pulling the probe 5 into the body of grain 6, but is intended to break frictional engagement between the probe 5 and the grain. The screw rod 30 and traveling nut assembly 40 provides the means for moving the drill string 4 up and down and is independent of rotation of the drill string 4.

In the illustrated example, the drill string 4 is composed of a plurality of preferably identical and easily handled lengths of drill pipe 58, which are preferably in the range of four to six feet each for ease of handling. Satisfactory results have been obtained with pipe in the range of one half inches to one and one half inches in diameter and the pipe may be either hollow or solid construction. The lengths of drill pipe 58 are interconnected by collars 59 and are conveniently connected by easily removeable and replaceable fasteners, such as bayonet pins 60 which extend through the collars 59 and the ends of the drill pipe 58 sleeved within the collars. The probe 5 connects to the lower end of the first section of drill pipe 58 to be mounted on the drill rig 3.

Two types of probes 5 are shown in connection with FIGS. 7 through 19 and include a sampler probe 64, FIGS. 7 through 12, and a dispenser probe 65, FIGS. 13 through 19. As indicated by their names, the sampler probe 64 operates to retrieve a sample of grain or other granular material and the dispenser probe 65 dispenses a quantity of a desired material, such as granular pesticide or insecticide. In the illustrated example, the sampler probe 64 is formed of a tubular shell 68 with a shaft 69 extending therethrough and connectible to the drill pipe 58. The tubular shell 68 is closed at top and bottom ends by rings 70 and 71, through which the shaft 69 extends. A bottom cone 72 is secured by a fastener 73 to a lower end of the shaft 69 situated adjacent the bottom ring 71 and that rotates relative to the ring 71. The rings 70 and 71 are affixed to the shaft 69 by external snap rings 74. An opening or receiving port or door 75 in the tubular shell 68 is situated adjacent a top end 76 of the probe 64 and an outer shell segment 78 is mounted over the top end 76 of the tubular shell 68 for a close tolerance slip fit. The outer shell segment 78 has a door 79 therein matching the door 75 to provide a closure means. The outer shell segment 78 rotates relative to the tubular shell 68 whereby the door 79 on the outer shell segment 78 aligns with the door 75 in the tubular shell 68 and permits entry of materials through the registered doors 75 and 79 into the interior of the tubular shell 68.

To aid in relative rotation, a vane 81, FIGS. 10, 11 and 12, is mounted to the side of the outer shell segment 78 opposite the door 79 and is aligned longitudinally with the length of the probe 64. The vane 81 contacts the grain outside of the probe 64 and exerts a drag or opposing force to cause the outer shell segment 78 to rotate relative to the inner tubular shell 68, and thereby cause the doors 75 and 79 to register or deregister as selected by the operator and controlled by direction of rotation of the drill string 4.

Stops are provided for the outer shell segment 78 and, in the illustrated example, include a stop ring 83, FIGS. 7, 8, and 9, secured to the exterior of the tubular shell 68 and situated immediately below the outer shell segment 78. The stop ring 83 has an upwardly extending tab 86 which protrudes and rides in an inset 88 formed in the bottom of the outer shell segment 78. Edge walls at the opposite termini of the inset 88 provide opening and closing stops 90 and 91 which, as the outer shell segment 78 rotates relative to the tubular shell 68 and the stop ring 83, contact the tab 86 to provide opposite limits of rotation of the outer shell segment 78. The stop ring 83 also provides a bottom slip support for the outer shell segment 78 to prevent it from slipping down.

In use, the sampler probe 64 is inserted in a body of grain 6 at a depth selected by the number of units of drill pipe 58 making up the drill string 4. As previously indicated, with the drill rig 3, this depth can extend down to eighty to one hundred thirty feet, or any lesser depth. Movement of the drill string 4, with the probe 64 attached to the end thereof, or at intervals therealong, FIG. 20, is accomplished by rotating the drill string 4, through the operation of the motor 46, and urging the drill string 4 downwardly by operation of the motor 38, causing rotation of the screw rod 30 and movement of the traveling nut assembly 40. As each successive length of drill pipe 58 is moved downwardly and bottoms against the floor plate 13, the coupling adjacent the U-joint connection 48 is detached and a new length of drill pipe 58 inserted until the desired depth within the body of grain 6 is reached.

As the sampler probe 64 is emplaced within the body of grain 6, movement is in a counter-clockwise direction, FIG. 10, whereby the stop ring tab 86 abuts the closing stop 90 and the doors 75 and 79 between the respective tubular shell 68 and outer shell segment 78 are out of registration to prevent entry of granular material into the interior of the tubular shell 68. When the desired depth is reached, rotation of the sampler probe 64 is reversed by manipulation of the control levers 55. The vane 81, engaging the grain, exerts a push in the opposite direction to the outer shell segment 78 and causes the segment 78 to rotate relative to the tubular shell 68 until the opening stop 90 of the segment 78 encounters the tab 86. At this point, the doors 75 and 79 are in registration with each other and, upon further rotation, FIG. 11, grain 6 for analysis is swept into the tubular shell 68.

To secure the tubular shell 68 against further entry of grain, rotation is again reversed to a counter-clockwise direction where upon the vane 81 engages the grain 6, spinning the outer shell segment 78 so that the closing stop 91 engages the stop ring tab 86 and the tubular shell 68 and the outer shell segment 78 rotate as a unitary structure, FIG. 12. Several episodes of this counter-clockwise/clockwise/counter-clockwise rotation may be utilized to place a number of slugs or batches 93 of grain 6 within the probe 64, FIG. 7, wherein each batch represents a sample taken at a selected level or depth within the body of grain.

For dispensing a granular fumigant into the body of grain at a selected depth, the dispenser probe 65 is utilized, FIGS. 13 through 19. In this embodiment, the dispenser probe 65 is inverted and fumigant pellets 94 are loaded into a bottom end 95 of the dispenser probe 65 and, through rotation into the body of grain, upon counter-rotation, the bottom end 95 opens and the fumigant pellets 94 spill downwardly into the body of grain.

In the illustrated embodiment, the dispenser probe 65 is formed of a shaft 98 sleeved within an elongate tubular shell 99. The shell 99 is closed at the top by a top ring 100 that is non-rotatably secured to the shaft 98 by a fastener 101, FIG. 14. A top end 102 of the tubular shell 99 slips over the ring 100 and rotates relative thereto. The top end 102 of the shell 99 includes a stop assembly 104, FIGS. 14 and 15, which limits rotation of the shell 99 relative to the shaft 98. In the illustrated example, the stop assembly 104 includes a ring 105 mounted below the top ring 100 and relatively rotatable thereto. The ring 105 does not rotate relative to the tubular shell 99 and is held fixed by fasteners 106. A bore 107 in the ring 105 receives a spring loaded pin 108 which extends and retracts within the bore 107, as urged by engagement with an underlying cam or ramp ring 109. The ramp ring 109 is secured to the shaft 98 by a fastener 111 and accordingly, the ramp ring 109 rotates relative to the overlying ring 105. The ramp ring 109 includes a cam surface or ramp slope 113 leading to a land area 115 terminating in an abutment wall 116 returning to the ramp slope 113.

Accordingly, the stop assembly 104 permits continuous respective rotation of the ramp ring 109 relative to the overlying ring 105 with the pin 108 retracting into the bore 107 as it progresses along the ramp slope 113 and again extending outwardly as it encounters the wall 116. Reverse rotation, such as counter-clockwise rotation, permits the pin 108 to abut the wall 116 and thereby limits counter-clockwise rotation to substantially one full turn.

A lower assembly 122 provides a selectively openable port or passage 123, FIG. 13, to permit expulsion of the fumigant pellets 94. In the illustrated example, the lower assembly 122 is in the form of a split ring unit and includes a closure means of a semi-circular ring section 125 which mates with a semi-circular conical section 126 that is secured by fasteners 127 to the interior surface of the tubular shell 99 at a lower end. A sloping wall 128 facilitates movement of the fumigant pellets out of the interior chamber of the shell 99. In the illustrated example, during counter-clockwise rotation of the drill string 4 and shaft 98, the upper assembly 122 is maintained in a closed position, FIG. 19. Upon reversal of rotation, or rotation in a clockwise direction, FIG. 13, the stop assembly 104 substantially freewheels and the lower assembly 122 alternately closes and opens, FIG. 13, to permit expulsion of the fumigant pellets. An auger flyte 130 mounted on the shaft 98 facilitates expulsion of the pellets.

The tubular shell 99 also includes an external vane 132 mounted longitudinally along its outer surface and which engages the grain to provide a drag sufficient to induce relative rotation between the shaft 98 and the shell 99.

In use, the dispenser probe 65 is packed with fumigant pellets, attached to the drill string 4 and drilled to a selected depth within the body of grain 6, using a counter-clockwise rotation. At the selected depth, rotation of the drill string 4 is reversed to a clockwise direction and fumigant is expelled through the passage 123 in the lower assembly 122 by the downward urging of the auger flyte 130. During the reversing or clockwise operation, the passage 123 alternately opens and closes as the stop assembly 104 freewheels.

It is to be understood that while one form of this invention has been illustrated and described, it it not to be limited to the specific form or arrangement of parts herein described and shown, except insofar as such limitations are included in the following claims.

What is claimed and desired to be secured by Letters Patent is as follows:

1. A probe insertable into a body of particulate material and comprising:
   (a) an inner shaft;
   (b) an outer probe body shell sleeved about said shaft and defining a container;
   (c) a door in said probe body shell for access to said container; and
   (d) means connected to said door and engageable with said particulate material, whereby when said shaft rotates in a selected direction, said means open said door.

2. A dispenser probe insertable into a body of particulate material and comprising:
   (a) an inner shaft;
   (b) an outer body shell rotatably sleeved about said inner shaft and having upper and lower ends;
   (c) said shell upper end being closed; and
   (d) said shell lower en having semi-circular ring segments respectively affixed to said shell and said shaft and relatively rotatable to provide a lower passage from said shell.

3. The dispenser probe set forth in claim 2 wherein:
   (a) said body shell includes an outer vane engageable with said particulate material.

4. The dispenser probe set forth in claim 2 wherein:
   (a) said inner shaft has an auger flyte thereon and positioned adjacent said shell lower end.

5. A grain drill and probe for insertion into a body of grain and comprising:
   (a) a support tower having a base and an upright post extending therefrom and mountable over an opening of a grain elevator bin; said base having clamp means therewith for clamping said support tower about said opening;
   (b) a hydraulic power unit providing pressurized fluid, and including controls for independent directional porting of said pressurized fluid;
   (c) a first hydraulic motor mounted on said support tower and operatively connected to a rotary screw shaft extending upright adjacent said post;
   (d) a traveling nut mounted on said screw shaft and moveable up and down, said traveling nut being joined to a traveling platform extending between said shaft and said post;
   (e) a second hydraulic motor mounted on said traveling platform and comprising a rotary head; said head connected to a joint fitting extending therefrom;
   (f) a plurality of lengths of drill string and couples for joining said drill string together and to said rotary head; said drill string being rotatable by operation of said rotary head and moveable into said body of grain by operation of said screw shaft and traveling nut and platform; and
   (g) a probe connected to said drill string for insertion into said body of grain.

6. The grain drill and probe set forth in claim 5 wherein:
   (a) said probe includes means for retrieving samples from said body of grain.

7. The grain drill and probe set forth in claim 5 wherein:
   (a) said probe includes means for depositing fumigant material in said body of grain.

8. A drill and probe for insertion into a body of particulate material and comprising:
   (a) support means maintainable relative to a bin means containing said particulate material;
   (b) a drill string;
   (c) means for simultaneously rotating and selectively urging said drill string into a body of grain;
   (d) a probe means connectible to said drill string and including a port normally closed by closure means including a door thereover; and
   (e) means opening and closing said door in response to opposite direction rotation of said drill string for entry or exit of materials from said probe.

9. Mechanism for inserting a material sampling or dispensing probe downwardly in an opening in the top of a material container, and comprising:
   (a) a support tower having a base extending across said opening and connectible to the top of the container surrounding the opening:
   (b) a rotary head mounted on said support tower;
   (c) means for moving said rotary head up and down;
   (d) a drill string connected to said rotary head and said means for moving said rotary head up and down;
   (e) means for simultaneously rotating and selectively urging said drill string downwardly;
   (f) a material sampling or dispensing probe connectible to a remote end of said drill string; and
   (g) means for selective independent operation of said rotary head and means for moving said rotary head whereby said drill string and probe are rotatable clockwise and counterclockwise while remaining at a selected depth in said material container.

* * * * *